United States Patent
Wessel et al.

(10) Patent No.: US 10,648,912 B2
(45) Date of Patent: May 12, 2020

(54) METHODS AND SYSTEMS FOR INSTRUMENT VALIDATION

(71) Applicant: LIFE TECHNOLOGIES CORPORATION, Carlsbad, CA (US)

(72) Inventors: Thomas Wessel, Pleasanton, CA (US); Yong Chu, Castro Valley, CA (US); Jacob Freudenthal, San Jose, CA (US); David Woo, Foster City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 863 days.

(21) Appl. No.: 15/016,485

(22) Filed: Feb. 5, 2016

(65) Prior Publication Data

US 2016/0231245 A1    Aug. 11, 2016

Related U.S. Application Data

(60) Provisional application No. 62/113,077, filed on Feb. 6, 2015.

(51) Int. Cl.
  *G01N 21/64* (2006.01)
  *G01N 21/27* (2006.01)
  *G16B 40/00* (2019.01)

(52) U.S. Cl.
  CPC ....... *G01N 21/6428* (2013.01); *G01N 21/274* (2013.01); *G01N 21/6452* (2013.01); *G01N 21/6456* (2013.01); *G01N 2021/6439* (2013.01); *G16B 40/00* (2019.02)

(58) Field of Classification Search
  None
  See application file for complete search history.

(56) References Cited

U.S. PATENT DOCUMENTS 7,630,849 B2    12/2009    DeSimas et al.
2012/0231458 A1    9/2012    Bae

FOREIGN PATENT DOCUMENTS

JP    2013533523 A    8/2013
WO    2011060240 A1    5/2011
WO    2012068276 A2    5/2012

OTHER PUBLICATIONS

Written Opinion issued in Singapore Application No. 11201706250V, dated May 24, 2018, pp. 1-5.
Applied Biosystems, TaqMan RNase P 96-Well Instrument Verification Plate, 2010, 3 pages, No. 4314333—Rev. F, Applied Biosystems.
Applied Biosystems, Data Analysis on the ABI PRISM 7700 Sequence Detection System: Setting Baselines and Thresholds, 2002, pp. 1-12, Applied Biosystems.
Amadio, M., Taq Man RNase P 96-Well Instrument Verification Plate, Product Insert, Jul. 31, 2001, 1 page, 4314333 Rev D, Applied Biosystems.

*Primary Examiner* — Joseph Woitach
(74) *Attorney, Agent, or Firm* — Mauriel Kapouytian Woods LLP; Liang Huang; Michael Mauriel

(57) ABSTRACT

In one exemplary embodiment, a method for validating an instrument is provided. The method includes receiving amplification data from a validation plate to generate a plurality of amplification curves. The validation plate includes a sample of a first quantity and a second quantity, and each amplification curve includes an exponential region. The method further includes determining a set of fluorescence thresholds based on the exponential regions of the plurality of amplification curves and determining, for each fluorescence threshold of the set, a first set of cycle threshold ($C_t$) values of amplification curves generated from the samples of the first quantity and a second set of $C_t$ values of amplification curves generated from the samples of the second quantity. The method includes calculating if the first and second quantities are sufficiently distinguishable based on $C_t$ values at each of the plurality of fluorescence thresholds.

20 Claims, 8 Drawing Sheets

METHODS AND SYSTEMS FOR INSTRUMENT VALIDATION

CROSS-REFERENCE TO RELATED APPLICATIONS

This application claims the benefit of priority of U.S. Provisional Patent Application No. 62/113,077, filed on Feb. 6, 2015, which is incorporated herein in its entirety by reference.

BACKGROUND

Installation and calibration of laboratory instrumentation can be a time consuming and expensive process. In many cases, engineers from the instrument supplier must be on site to perform these processes. This cost is generally passed on to the user. In some cases, experienced users can successfully calibrate properly manufactured instruments using multi-step procedures. During such calibration, physical standards and well plates may be used in combination with manual procedures. Manual calibration processing and data inspection is error prone and may rely on ad hoc or subjective measures. While a final system verification step may provide resilience against accepting suboptimal calibrations, automation offers improved objectivity and uniformity during such activities.

After installation and after several uses, it is important to validate that the instrument is working properly. Often, a user will manually run a known assay to validate an instrument, such as an RNase P assay.

In a traditional RNase P assay example, a standard curve is generated from the Ct (cycle threshold) values obtained from a set of replicate standards (1,250, 2,500, 5,000, 10,000 and 20,000 copies). The standard curve is then used to determine the copy number for two sets of unknown templates (5,000 and 10,000 replicate populations). The instrument is validated if it can demonstrate the ability to distinguish between 5,000 and 10,000 genomic equivalents with a 99.7% confidence level for a subsequent sample run in a single well.

SUMMARY

In one exemplary embodiment, a method for validating an instrument is provided. The method includes receiving amplification data from a validation plate to generate a plurality of amplification curves. The validation plate includes a sample of a first quantity and a second quantity, and each amplification curve includes an exponential region. The method further includes determining a set of fluorescence thresholds based on the exponential regions of the plurality of amplification curves and determining, for each fluorescence threshold of the set, a first set of cycle threshold ($C_t$) values of amplification curves generated from the samples of the first quantity and a second set of $C_t$ values of amplification curves generated from the samples of the second quantity. The method includes calculating if the first and second quantities are sufficiently distinguishable based on $C_t$ values at each of the plurality of fluorescence thresholds.

In another exemplary embodiment, a computer-readable storage medium encoded with processor-executable instructions for validating an instrument is provided. The instructions comprise instructions for receiving amplification data from a validation plate to generate a plurality of amplification curves. The validation plate includes a sample of a first quantity and a second quantity, and each amplification curve includes an exponential region. The instructions further comprise instructions for determining a set of fluorescence thresholds based on the exponential regions of the plurality of amplification curves and determining, for each fluorescence threshold of the set, a first set of cycle threshold ($C_t$) values of amplification curves generated from the samples of the first quantity and a second set of $C_t$ values of amplification curves generated from the samples of the second quantity. The instructions comprise instructions for calculating if the first and second quantities are sufficiently distinguishable based on $C_t$ values at each of the plurality of fluorescence thresholds.

In another exemplary embodiment, a system for validating an instrument is provided. The system includes a processor and a memory configured to store processor-executable instructions. The instructions include instructions for receiving amplification data from a validation plate to generate a plurality of amplification curves. The validation plate includes a sample of a first quantity and a second quantity, and each amplification curve includes an exponential region. The instructions further include instructions for determining a set of fluorescence thresholds based on the exponential regions of the plurality of amplification curves and determining, for each fluorescence threshold of the set, a first set of cycle threshold ($C_t$) values of amplification curves generated from the samples of the first quantity and a second set of $C_t$ values of amplification curves generated from the samples of the second quantity. The instructions include instructions for calculating if the first and second quantities are sufficiently distinguishable based on $C_t$ values at each of the plurality of fluorescence thresholds.

In another exemplary embodiment, a system for validating an instrument is provided. The system includes a PCR instrument interface configured to receive amplification data from a validation plate to generate a plurality of amplification curves. The validation plate includes a sample of a first quantity and a second quantity, and each amplification curve includes an exponential region. The system further includes a (cycle threshold) $C_t$ calculator configured to: determine a set of fluorescence thresholds based on the exponential regions of the plurality of amplification curves, and determine, for each fluorescence threshold of the set, a first set of $C_t$ values of amplification curves generated from the samples of the first quantity and a second set of $C_t$ values of amplification curves generated from the samples of the second quantity. The system includes a $C_t$ database configured to store the first and second set of $C_t$ values for each fluorescence threshold of the set. The system further includes a validator configured to calculate if the first and second quantities are sufficiently distinguishable based on $C_t$ values at each of the plurality of fluorescence thresholds.

DETAILED DESCRIPTION

Figure 1:
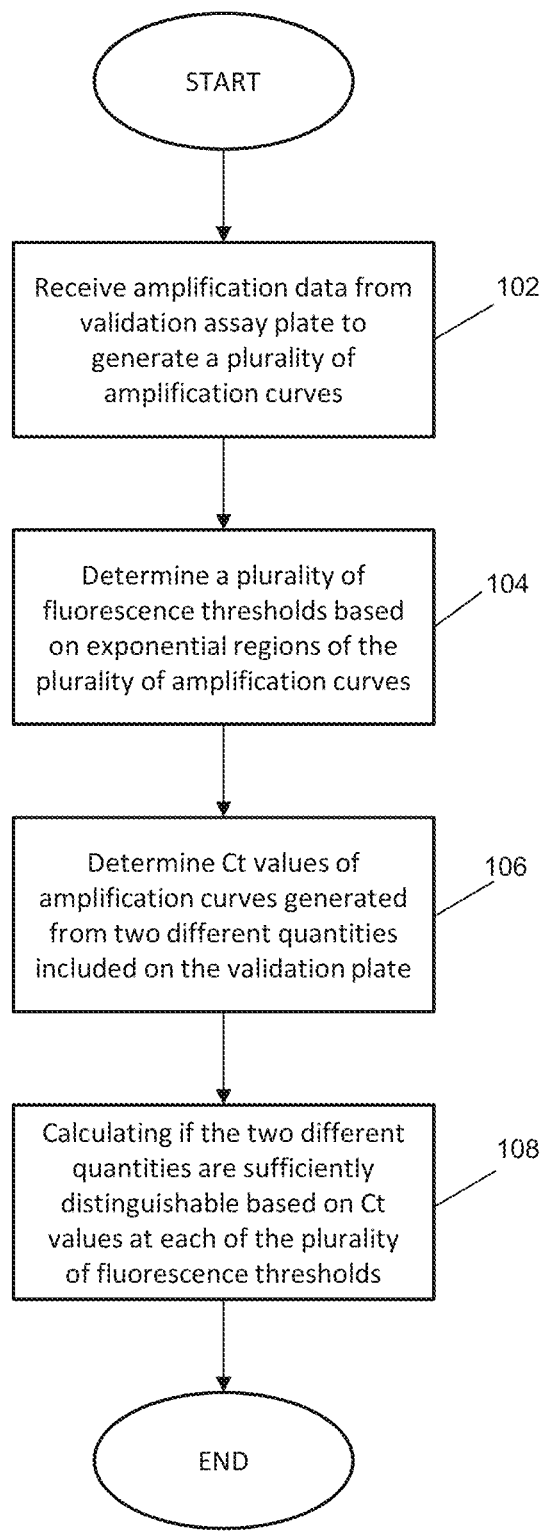
FIG. 1 illustrates an exemplary method for validating an instrument according to various embodiments described herein.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

As mentioned above, it is important to validate an instrument to be sure it is working properly especially after a new installation or after several uses. In this way, a user may be sure experimental results and analyses are accurate and reliable. Previously, a validation assay was run on the instrument by a user and the user manually performed data analysis on the amplification data from the verification assay to validate the instrument. Because the data analysis was performed manually by the user, the validation process was more prone to error and took time.

According to various embodiments of the present teachings, automated validation methods and systems are provided. An example of a validation assay is an RNase P assay. However, as used herein, validation assay may be any assay that has known and reliable properties and can be used to validate an instrument.

After installation and after several uses, it is important to validate that the instrument is working properly. Often, a user will manually run a known assay to validate an instrument, such as an RNase P assay. The RNase P gene is a single-copy gene encoding the RNA moiety of the RNase P enzyme. It is often used as a validation assay because of its known properties and characteristics.

A validation plate is preloaded with the reagents necessary for the detection and quantitation of genomic copies of the sample. For example, in an RNase P validation plate, each well contains PCR master mix, RNase P primers, FAM™ dye-labeled probe, and a known concentration of human genomic DNA template.

In a traditional RNase P assay example, a standard curve is generated from the Ct (cycle threshold) values obtained from a set of replicate standards (1,250, 2,500, 5,000, 10,000 and 20,000 copies). The standard curve is then used to determine the copy number for two sets of unknown templates (5,000 and 10,000 replicate populations). The instrument is validated if it can demonstrate the ability to distinguish between 5,000 and 10,000 genomic equivalents with a 99.7% confidence level for a subsequent sample run in a single well.

To pass installation, the instruments must demonstrate the ability to distinguish between 5,000 and 10,000 genomic equivalents with a 99.7% confidence level for a subsequent sample run in a single well.

According to various embodiments, the present teachings can incorporate expert knowledge into an automated calibration and validation system providing pass/fail status and troubleshooting feedback when a failure is identified. If an instrument should fail the validation process, then the user knows that a service engineer can be called, for example. The present teachings can minimize the cost of, and time required for, the installation and calibration procedures.

As stated above, according to various embodiments described herein, the goal of a validation analysis is to confirm that two quantities of the same sample are sufficiently distinguishable by the instrument. This way, the instrument performance may be validated.

According to various embodiments of the present teachings, an automated validation method and system is provided. Cycle threshold values ($C_t$s) of a validation assay are analyzed and compared by a system to determine if an instrument can sufficiently distinguish two quantities of a sample. An example of a validation assay is the RNase P assay. In this example, a system determines $C_t$ values generated for RNase P samples of 5000 and 10000 genomic copies to determine if the data from the 5000 and 10000 genomic copies are sufficiently distinguishable. Sufficiently distinguishable, according to the embodiments described herein, means at least 3 standard deviations ($3\sigma$) ($\sim$99.7%) separate the 5000 and 10000 genomic copy amplification data. The method according to various embodiments is described further below with reference to FIGS. 1 and 2.

FIG. 1 illustrates an exemplary method for validating an instrument according to various embodiments described herein. In general, the begins in step 102 by receiving amplification data from a validation assay plate to generate a plurality of amplification curves, each corresponding to a well on the plate.

Plates contain a plurality of wells. In some examples, a plate contains 96 wells. In other examples, a plate contains 384 wells. A portion of the wells in the plate may contain a sample of a first quantity and another portion of the wells in the plate may contain a sample of a second quantity. The first quantity and the second quantity are different. The second quantity is greater than the first quantity in various embodiments described herein. The second quantity may be a 1.5 fold difference than the first quantity in some embodiments. In other embodiments, the second quantity may be a 2 fold difference than the first quantity. According to various embodiments described herein, the second quantity may be any fold difference than the first quantity. In some embodiments, the first quantity may be 5000 genomic copies per well and the second quantity may be 10000 genomic copies per well.

With reference back to FIG. 1, in step 104, a plurality of fluorescence thresholds are determined based on the plurality of generated amplification curves. Exponential regions of the plurality of amplification curves are compared to determine a range of fluorescence values where the exponential regions fall. For example, the range of fluorescence values from the lowest fluorescence value of a bottom of an exponential region to the highest fluorescence value of a top of an exponential region of the plurality of amplification curves is determined. The fluorescence value range is used in the automated analysis of the plurality of amplification curves to validate the instrument according to embodiments of the present teachings.

Figure 3:
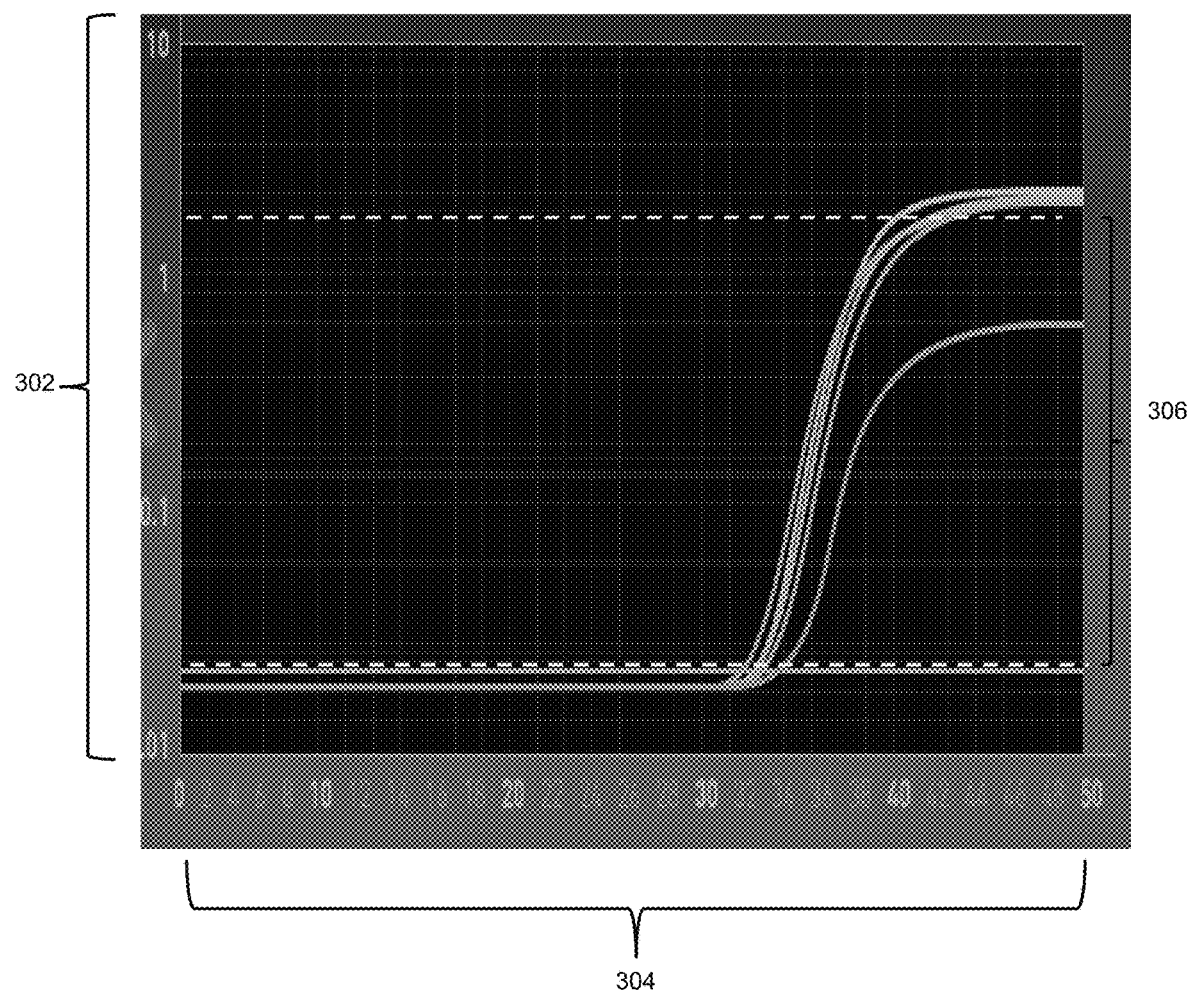
FIG. 3 illustrates determining a plurality of fluorescence thresholds from amplification data according to various embodiments described herein.

With reference to FIG. 3, a plurality of amplification curves and determination of a range of fluorescence values and corresponding cycle threshold is illustrated. Each of the plurality of amplification curves includes an exponential region of the curve. Axis 302 indicates fluorescence values. Axis 304 illustrates cycle numbers. Fluorescence range 306 shows the range of fluorescence values from the lowest fluorescent value of a determined bottom of an exponential region of the plurality of exponential regions and highest fluorescent value of a determined top of an exponential region of the plurality of exponential regions. According to various embodiments, the range of fluorescence values is divided evenly by a predetermined number to generate a set of fluorescence values for automated analysis by the system. In one example, the range of fluorescence values 306 is divided by 100 to determine 100 fluorescence values for a set of fluorescence thresholds. In some embodiments, the top 5 fluorescence values and the bottom 5 fluorescence values are discarded so that analysis proceeds with a set of 90 fluorescence thresholds.

With reference back to FIG. 1, in step 106, for each fluorescence value of the set of fluorescence values, the cycle threshold ($C_t$) is determined for each of the plurality of amplification curves generated from wells containing the first quantity of the sample. Similarly, for each fluorescence value of the set of fluorescence values, the cycle threshold ($C_t$) is determined for each of the plurality of amplification curves generated from wells containing the second quantity of the sample.

In step 108, using the $C_t$ values for the first and second quantities for each of the fluorescence values of the set, it is determined if the first and second quantities are sufficiently distinguishable. Sufficiently distinguishable, according to various embodiments, means that, using equation (1), yields a positive result for at least one of the fluorescence values of the set:

$$((\mu C_{tquant1} - 3\sigma C_{tquant1}) - (\mu C_{tquant2} + 3\sigma C_{quant2})) \quad (1)$$

Equation 1 determines if a first and second quantity are sufficiently distinguishable, where quant2 is greater than quant1, according to the embodiments described herein. Sufficiently distinguishable means at least 3 standard deviations ($3\sigma$) (~99.7%) separate the $C_t$ values of the first and second quantities. If it is found that the quantities are sufficiently distinguishable, an indication is provided to the user that the instrument is validated.

Figure 2:
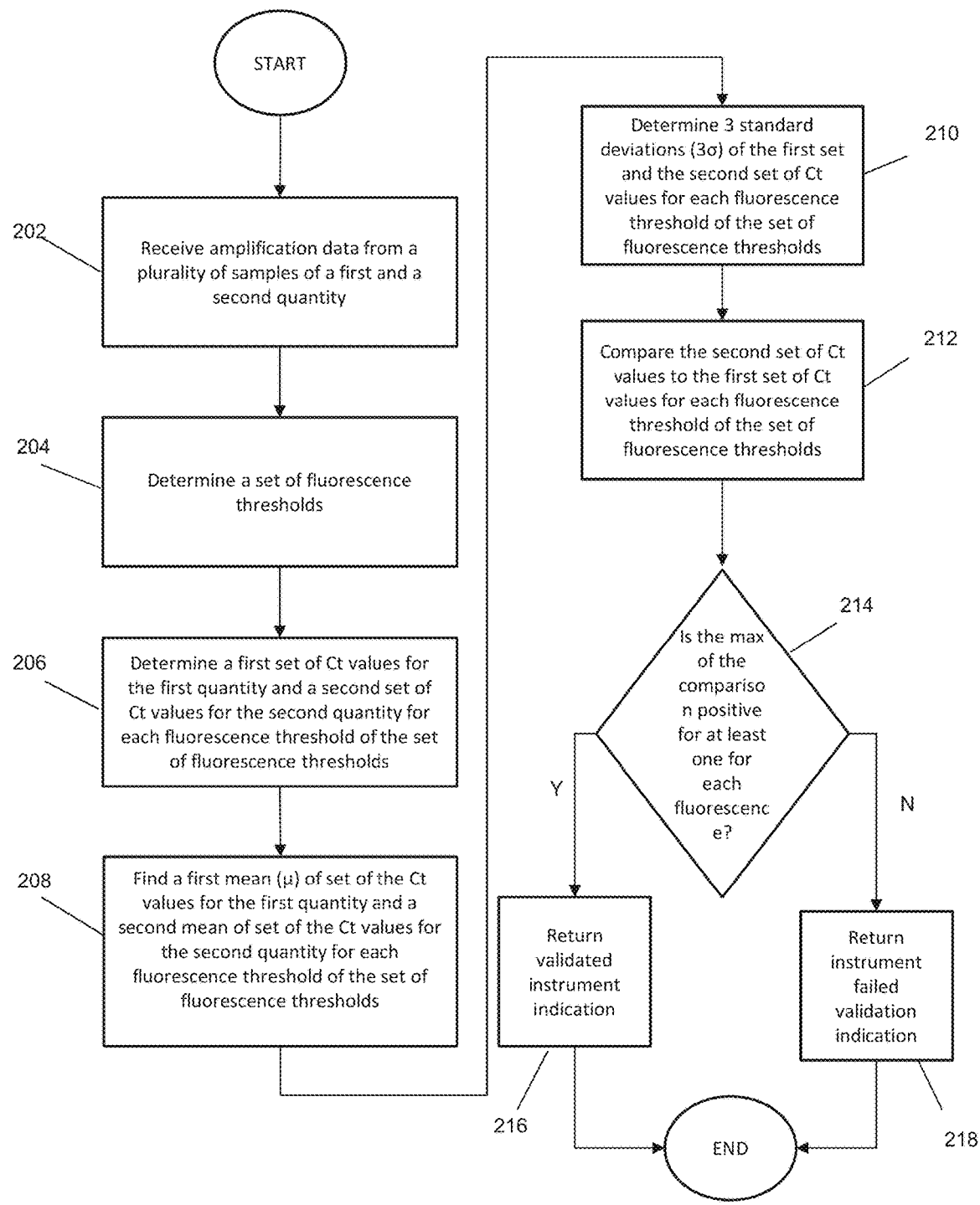
FIG. 2 illustrates another exemplary method for validation an instrument according to various embodiments described herein.

FIG. 2 illustrates another exemplary method for validation an instrument according to various embodiments described herein. In step 202, amplification data is received from a plurality of samples included in wells of a validation plate. A portion of the wells in the validation plate contain a sample in a first quantity. Another portion of the wells of the validation plate contain the sample in a second quantity. The first quantity and the second quantity are different. The second quantity is greater than the first quantity in various embodiments described herein. The second quantity may be a 1.5 fold difference than the first quantity in some embodiments. In other embodiments, the second quantity may be a 2 fold difference than the first quantity. According to various embodiments described herein, the second quantity may be any fold difference than the first quantity. In some embodiments, the first quantity may be 5000 genomic copies per well and the second quantity may be 10000 genomic copies per well.

In step 204, a first set of fluorescence thresholds are determined based on the plurality of generated amplification curves. Exponential regions of the plurality of amplification curves are compared to determine a range of fluorescence values where the exponential regions fall. For example, the range of fluorescence values from the lowest fluorescence value of a bottom of an exponential region to the highest fluorescence value of a top of an exponential region of the plurality of amplification curves is determined. The fluorescence value range is used in the automated analysis of the plurality of amplification curves to validate the instrument according to embodiments of the present teachings.

According to various embodiments, the range of fluorescence values is divided evenly by a predetermined number to generate a set of fluorescence values for automated analysis by the system. In one example, the range of fluorescence values 306 is divided by 100 to determine 100 fluorescence values for a set of fluorescence thresholds. In some embodiments, the top 5 fluorescence values and the bottom 5 fluorescence values are discarded so that analysis proceeds with a set of 90 fluorescence thresholds.

In step 206, for each fluorescence threshold of the set, a first set of $C_t$ values for the amplification curves corresponding to the first quantity is determined. Similarly, for each fluorescence threshold of the set, a second set of $C_t$ values for the amplification curves corresponding to the first quantity is determined. This is repeated for every fluorescence threshold in the set.

In some embodiments, a predetermined number of outlier $C_t$ values are removed from each set of $C_t$ values before further calculations are performed. For example, in some embodiments, if a 96 well plate is used, 6 outliers are removed from each set of $C_t$ values. An outlier is the $C_t$ values furthest away from the mean value of the set of $C_t$ values. In another example, if a 364 well plate is used, 10 outliers are removed from each set of $C_t$ values. After the outliers are removed, the remaining $C_t$ values of each set are used in the remaining steps of the method.

In step 208, for each set of $C_t$ values, a mean is calculated. In other words, a first $C_t$ mean is calculated for the first quantity amplification curves and a second $C_t$ mean is calculated for the second quantity amplification curves for each fluorescence threshold of the set determined in step 204.

Similar to step 208, in step 210, 3 standard deviations of each set of $C_t$ values is calculated. In other words, a first 3 standard deviations is calculated for the first quantity amplification curves and a second 3 standard deviations is calculated for the second quantity amplification curves for each fluorescence threshold of the set determined in step 204.

To determine if the $C_t$ values of the first quantity and the second quantity are sufficiently distinguishable, the $C_t$ values at a fluorescence value, according to various embodiments, are compared. According to various embodiments, equation (1) is used for the comparison.

$$((\mu C_{tquant1} - 3\sigma C_{tquant1}) - (\mu C_{tquant2} + 3\sigma C_{tquant2})) \quad (1)$$

Equation 1 determines if a first and second quantity are sufficiently distinguishable, where quant2 is greater than quant1, according to the embodiments described herein. Sufficiently distinguishable means at least 3 standard deviations ($3\sigma$) (~99.7%) separate the $C_t$ values of the first and second quantities.

In step 214, the results of equation (2) for all fluorescence thresholds of the set are compared to determine a maximum value. If the maximum value is a positive number, the instrument can sufficiently distinguish between the first and second quantity and an indication that the instrument is validated is provided to the user in step 216. If the maximum value is a negative number, the instrument cannot sufficiently distinguish between the first and second quantity and an indication the instrument failed validation is provided to the user in step 218.

Figure 4:
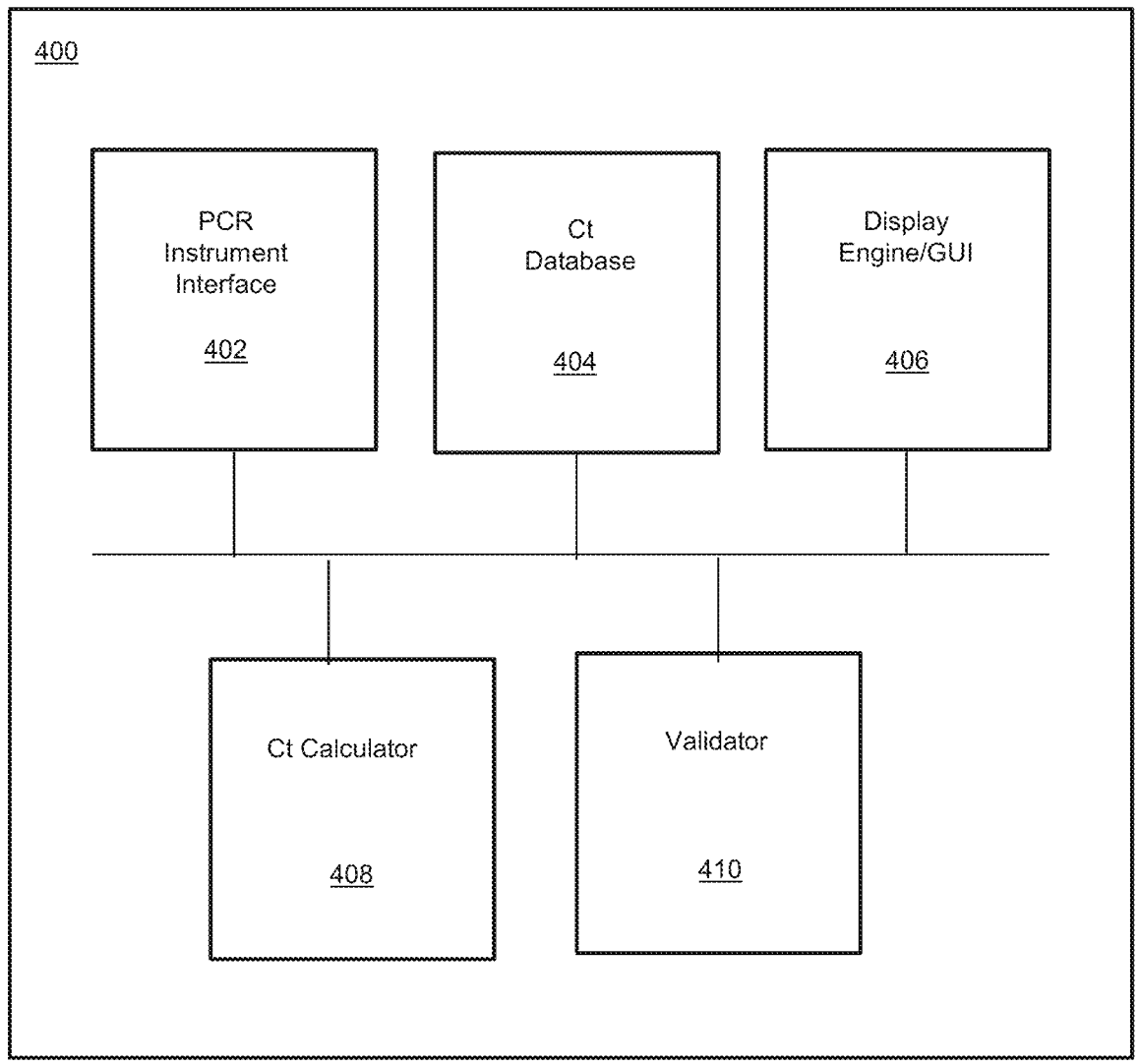
FIG. 4 illustrates a system for validation of an instrument according to various embodiments described herein.

FIG. 4 illustrates system 400 for validation of an instrument according to various embodiments described herein.

System 400 includes PCR instrument interface 402, $C_t$ database 404, display engine/GUI 406, $C_t$ calculator 408, and validator 410.

PCR instrument interface 402 receives the amplification data from the PCR instrument to generate amplification curves. As described above, the PCR instrument amplifies the samples contained in the validation plate. The validation plate includes a portion of wells containing a sample of a first quantity and another portion of wells containing a sample of a second quantity. Fluorescence data generated from amplification of the samples is received by PCR instrument interface 402.

After a set of fluorescence thresholds are determined as in steps 104 and 204, with reference to FIGS. 1 and 2, respectively, $C_t$ calculator 406 calculates a first and second set of $C_t$ values corresponding to the amplification curves generated from the samples of the first quantity and the second quantity, respectively. A first and second set of $C_t$ values is calculated for each fluorescence threshold in the set of fluorescence thresholds. The plurality of sets of $C_t$ values are stored in $C_t$ database 404.

Validator 410 determines whether the first and second quantities are sufficiently distinguishable as described in step 108 in FIG. 1 and steps 210 and 212 in FIG. 2.

Display engine/GUI displays the plurality of amplification curves to the user. Further, after validator 410 determines whether the first and second quantities are sufficiently distinguishable, display engine/GUI 406 displays an indication of validation or failed validation to the user.

Furthermore, an optimal fluorescence threshold can be determined. The optimal fluorescence threshold may be determined by, according to various embodiments, selecting the Ct value that resulting in the maximum separation between ($\mu C_{tquant1} - 3\sigma_{tquant1}$) and ($\mu C_{tquant2} + 3\rho C_{tquant2}$). Moreover, the optimal fluorescence threshold may also be selected based on the Ct value which resulted in the fewest number of determined outliers. The optimal fluorescence threshold may also be selected based on the Ct value which resulted in the maximum separation between ($\mu C_{quant1} - 3\sigma_{tquant1}$) and ($\mu C_{quant2} + 3\sigma C_{tquant2}$) and with the fewest number of determined outliers.

Computer-Implemented System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 5:
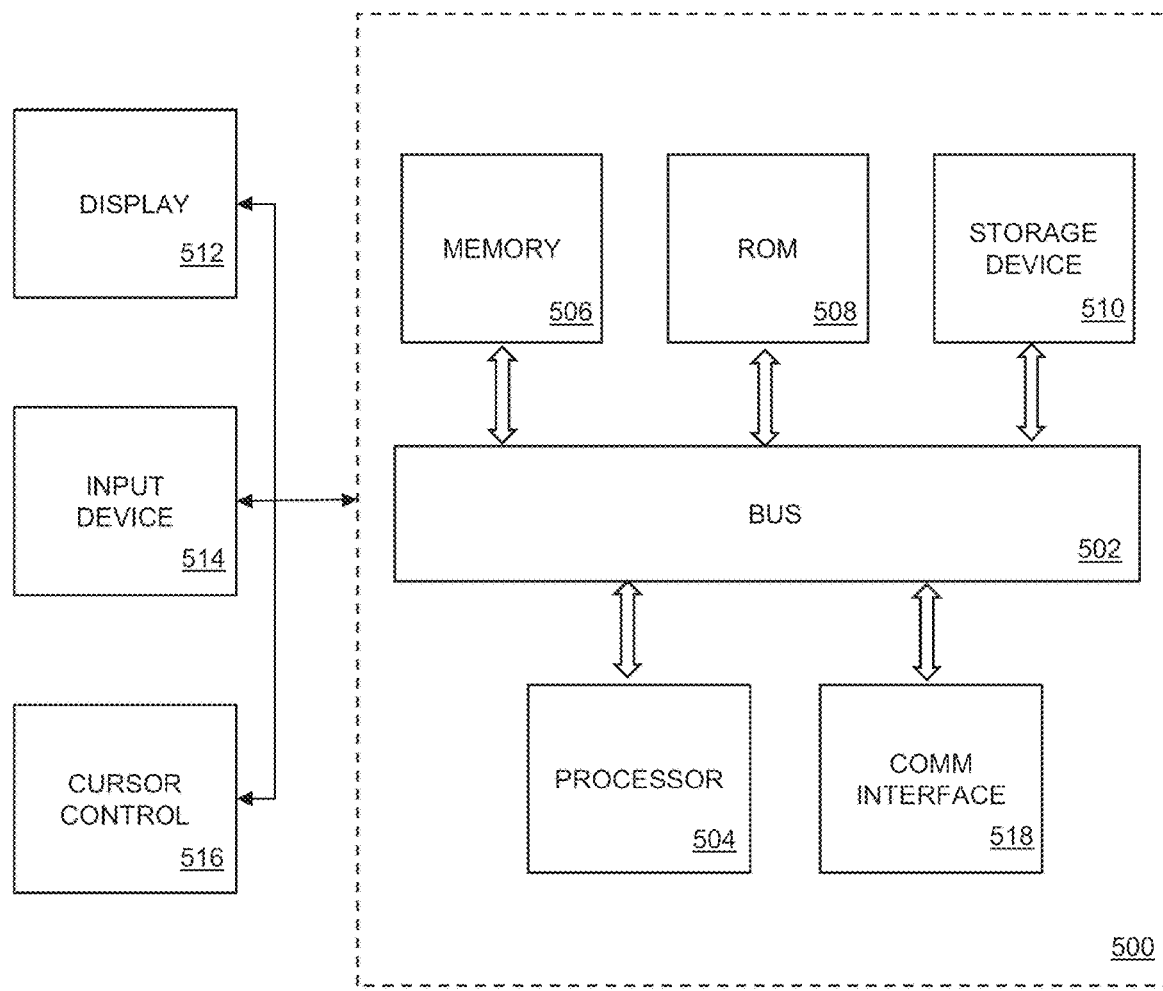
FIG. 5 illustrates an exemplary computing system for implementing various embodiments described herein.

FIG. 5 is a block diagram that illustrates a computer system 500 that may be employed to carry out processing functionality, according to various embodiments. Instruments to perform experiments may be connected to the exemplary computing system 500. Computing system 500 can include one or more processors, such as a processor 504. Processor 504 can be implemented using a general or special purpose processing engine such as, for example, a microprocessor, controller or other control logic. In this example, processor 504 is connected to a bus 502 or other communication medium.

Further, it should be appreciated that a computing system 500 of FIG. 5 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 500 may be configured to connect to one or more servers in a distributed network. Computing system 500 may receive information or updates from the distributed network. Computing system 500 may also transmit information to be stored within the distributed network that may be accessed by other clients connected to the distributed network.

Computing system 500 may include bus 502 or other communication mechanism for communicating information, and processor 504 coupled with bus 502 for processing information.

Computing system 500 also includes a memory 506, which can be a random access memory (RAM) or other dynamic memory, coupled to bus 502 for storing instructions to be executed by processor 504. Memory 506 also may be used for storing temporary variables or other intermediate information during execution of instructions to be executed by processor 504. Computing system 500 further includes a read only memory (ROM) 508 or other static storage device coupled to bus 502 for storing static information and instructions for processor 504.

Computing system 500 may also include a storage device 510, such as a magnetic disk, optical disk, or solid state drive (SSD) is provided and coupled to bus 502 for storing information and instructions. Storage device 510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 510 may include other similar instrumentalities for allowing computer programs or other instructions or data to be loaded into computing system 500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 510 to computing system 500.

Computing system 500 can also include a communications interface 518. Communications interface 518 can be used to allow software and data to be transferred between computing system 500 and external devices. Examples of communications interface 518 can include a modem, a network interface (such as an Ethernet or other NIC card), a communications port (such as for example, a USB port, a RS-232C serial port), a PCMCIA slot and card, Bluetooth, etc. Software and data transferred via communications interface 518 are in the form of signals which can be electronic, electromagnetic, optical or other signals capable of being received by communications interface 518. These signals may be transmitted and received by communications interface 518 via a channel such as a wireless medium, wire or cable, fiber optics, or other communications medium. Some examples of a channel include a phone line, a cellular phone link, an RF link, a network interface, a local or wide area network, and other communications channels.

Computing system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504, for example. An input device may also be a display, such as an LCD display, configured with touchscreen input capabilities. Another type of user input device is cursor control 516, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. A computing system 500 provides data processing and provides a level of confidence for such data. Consistent with certain implementations of embodiments of the present teachings, data processing and confidence values are provided by computing system 500 in response to processor 504 executing one or more sequences of one or more instructions contained in memory 506. Such instructions may be read into memory 506 from another computer-readable medium, such as storage device 510. Execution of the sequences of instructions contained in memory 506 causes processor 504 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 504 for execution. Such instructions, generally referred to as "computer program code" (which may be grouped in the form of computer programs or other groupings), when executed, enable the computing system 500 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 510. Volatile media includes dynamic memory, such as memory 506. Transmission media includes coaxial cables, copper wire, and fiber optics, including the wires that comprise bus 502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computing system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 506, from which processor 504 retrieves and executes the instructions. The instructions received by memory 506 may optionally be stored on storage device 510 either before or after execution by processor 504.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Distributed System

Figure 6:
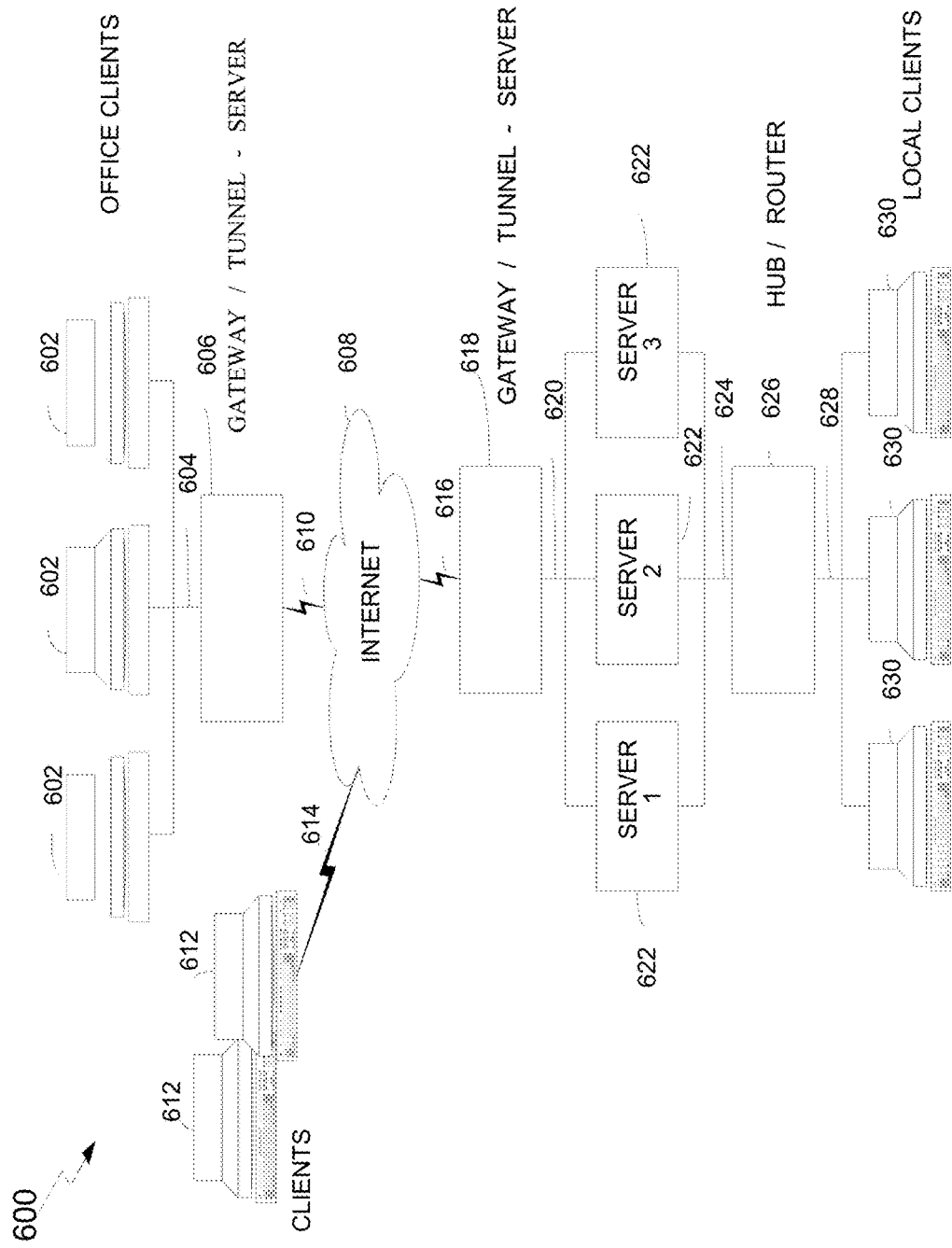
FIG. 6 illustrates an exemplary distributed network system according to various embodiments described herein.

Some of the elements of a typical Internet network configuration 600 are shown in FIG. 6, wherein a number of client machines 602 possibly in a remote local office, are shown connected to a gateway/hub/tunnel-server/etc 610 which is itself connected to the internet 608 via some internet service provider (ISP) connection 610. Also shown are other possible clients 612 similarly connected to the internet 608 via an ISP connection 614, with these units communicating to possibly a central lab or office, for example, via an ISP connection 616 to a gateway/tunnel-server 618 which is connected 620 to various enterprise application servers 622 which could be connected through another hub/router 626 to various local clients 630. Any of these servers 622 could function as a development server for the analysis of potential content management and delivery design solutions as described in the present invention, as more fully described below.

The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously measuring signals from a plurality of samples or spots for analytical purposes and often require calibration, including but not limited to processes involving: identifying ROI (Regions of Interest), determining background signal, uniformity and pure dye spectral calibration for multicomponent analysis. Calibration may also involve a RT-PCR validation reaction using a known sample plate with an expected outcome. One skilled in the art will appreciate that while the present teachings have been described with examples pertaining to RT-PCR instruments, their principles are widely applicable to other forms of laboratory instrumentation that may require calibration and verification in order to ensure accuracy and/or optimality of results.

PCR Instruments

Figure 7:
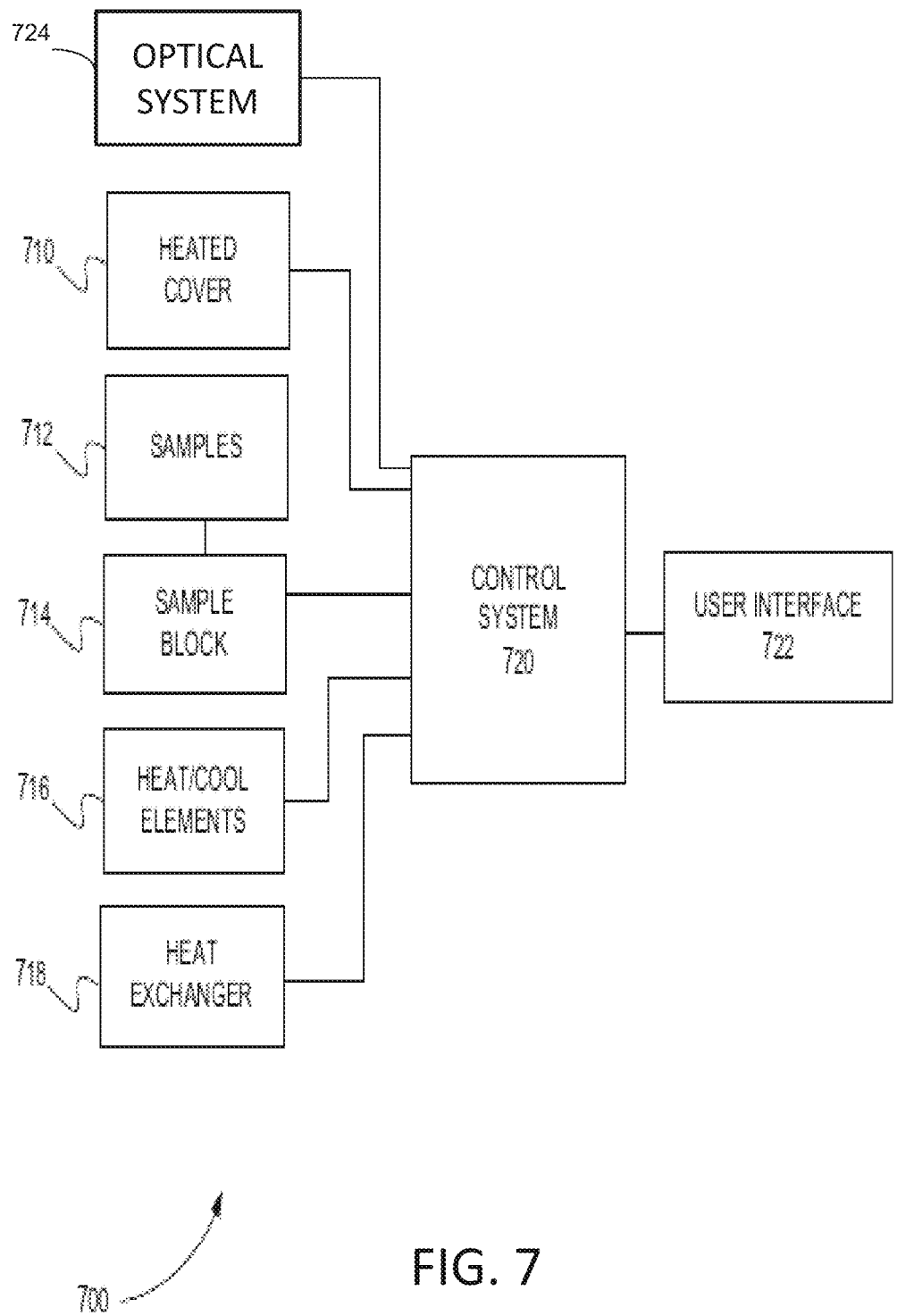
FIG. 7 is a block diagram that illustrates a PCR instrument 700 upon which embodiments of the present teachings may be implemented.

As mentioned above, an instrument that may be utilized according to various embodiments, but is not limited to, is a polymerase chain reaction (PCR) instrument. FIG. 7 is a block diagram that illustrates a PCR instrument 700, upon which embodiments of the present teachings may be implemented. PCR instrument 700 may include a heated cover 710 that is placed over a plurality of samples 712 contained in a substrate (not shown). In various embodiments, a substrate may be a glass or plastic slide with a plurality of sample regions, which sample regions have a cover between the sample regions and heated cover 710. Some examples of a substrate may include, but are not limited to, a multi-well plate, such as a standard microtiter 96-well, a 384-well plate, or a microcard, or a substantially planar support, such as a glass or plastic slide. The reaction sites in various embodiments of a substrate may include depressions, indentations, ridges, and combinations thereof, patterned in regular or irregular arrays formed on the surface of the substrate. Various embodiments of PCR instruments include a sample block 714, elements for heating and cooling 716, a heat exchanger 718, control system 720, and user interface 722. Various embodiments of a thermal block assembly according to the present teachings comprise components 714-718 of PCR instrument 700 of FIG. 7.

Real-time PCR instrument 700 has an optical system 724. In FIG. 7, an optical system 724 may have an illumination source (not shown) that emits electromagnetic energy, an optical sensor, detector, or imager (not shown), for receiving electromagnetic energy from samples 712 in a substrate, and optics 740 used to guide the electromagnetic energy from each DNA sample to the imager. For embodiments of PCR instrument 700 in FIG. 7 and real-time PCR instrument 700 in FIG. 7, control system 720, may be used to control the functions of the detection system, heated cover, and thermal block assembly. Control system 720 may be accessible to an end user through user interface 722 of PCR instrument 700 in FIG. 7 and real-time PCR instrument 700 in FIG. 7. Also a computer system 700, as depicted in FIG. 7, may serve as to provide the control the function of PCR instrument 700 in FIG. 7, as well as the user interface function. Additionally, computer system 500 of FIG. 5 may provide data processing, display and report preparation functions. All such instrument control functions may be dedicated locally to the PCR instrument, or computer system 500 of FIG. 5 may provide remote control of part or all of the control, analysis, and reporting functions, as will be discussed in more detail subsequently.

Optical System for Imaging

Figure 8:
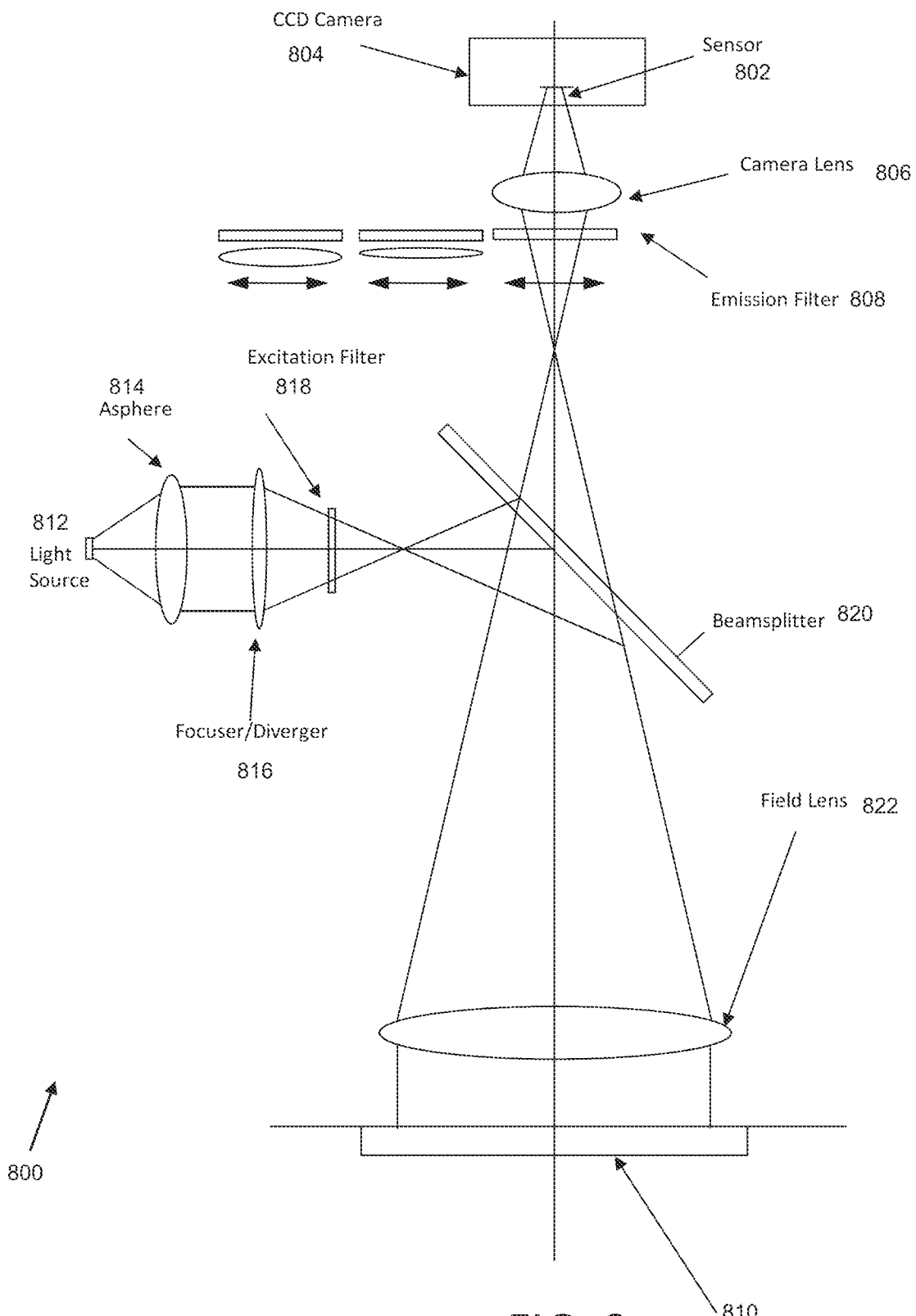
FIG. 8 depicts an exemplary optical system 300 that may be used for imaging according to embodiments described herein.

FIG. 8 depicts an exemplary optical system 800 that may be used for imaging according to embodiments described herein. It should be recognized that optical system 800 is an exemplary optical system and one skilled in the art would recognize that other optical systems may be used to capture images an object-of-interest. According to various embodiments, an object of interest may be a sample holder such as, for example, a calibration plate as described herein. An optical sensor 802 included in a camera 804, for example, may image an object-of-interest 810. The optical sensor 802 may be a CCD senor and the camera 804 may be a CCD camera. Further, the optical sensor includes a camera lens 806.

Depending on the object of interest, an emission filter 808 can be chosen for imagining the object-of-interest 810 according to various embodiments. Emission filter 808 may be changed to image fluorescent emission emitted from the object-of-interest 801 in other embodiments.

Optical system 800 may use a reflected light source 812 to image object-of-interest 810. The light from light source 812 may be filtered through an asphere 814, a focuser/diverger 816, and excitation filter 818 before being reflected to the object-of-interest 810 by beamsplitter 820. Optical system 800 may also include a field lens 822. Depending on the object of interest, the excitation filter 818 can be chosen or changed for imagining the object-of-interest 810 according to various embodiments.

In example 1, a method for validating an instrument is provided. The method comprises: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In alternate example 2, the method of example 1, further comprises displaying an indication the instrument is validated if the first and second quantities are sufficiently distinguishable.

In alternate example 3, the method of example 1 is provided, wherein the calculating if the first and second quantities are sufficiently distinguishable includes determining a mean ($\mu$) and a standard deviation ($\sigma$) of the first and second set of $C_t$ values.

In alternate example 4, the method of example 3 is provided, wherein the first and second quantities are sufficiently distinguishable if the following equation results in a positive number:

$$((\mu C_{tquant1} - 3\sigma C_{tquant1}) - (\mu C_{tquant2} + 3\sigma C_{tquant2})).$$

In alternate example 5, the method of example 1 is provided, wherein the sample is a RNase P gene.

In alternate example 6, the method of example 1 is provided, wherein the first and second quantity are different.

In alternate example 7, the method of example 1 is provided, wherein there is a 2-fold difference between the second quantity and the first quantity.

In alternate example 8, the method of example 1 is provided, wherein the first and second quantities are sufficiently distinguishable if the equation results in a positive number for at least one fluorescence threshold.

In alternate example 9, the method of example 1 is provided, further comprising: discarding a predetermined number of outliers from the first and second set of $C_t$ values.

In alternate example 10, the method of example 1 is provided, wherein the set of fluorescence thresholds includes 90 fluorescence thresholds.

In example 11, a computer-readable storage medium encoded with processor-executable instructions for validating an instrument is provided. The instructions comprising instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In alternate example 12, the computer-readable storage medium of example 11 is provided, further comprising instructions for: displaying an indication the instrument is validated if the first and second quantities are sufficiently distinguishable.

In alternate example 13, the computer-readable storage medium of example 11 is provided, wherein the instruction for calculating if the first and second quantities are sufficiently distinguishable includes determining a mean ($\mu$) and a standard deviation ($\sigma$) of the first and second set of $C_t$ values.

In alternate example 14, the computer-readable storage medium of example 13 is provided wherein the first and second quantities are sufficiently distinguishable if the following equation results in a positive number:

$$((\mu C_{tquant1} - 3\sigma C_{tquant1}) - (\mu C_{tquant2} + 3\sigma C_{tquant2})).$$

In alternate example 15, the computer-readable storage medium of example 11 is provided, wherein the sample is a RNase P gene.

In alternate example 16, the computer-readable storage medium of example 11 is provided, wherein the first and second quantity are different.

In alternate example 17, the computer-readable storage medium of example 11 is provided, wherein there is a 2-fold difference between the second quantity and the first quantity.

In alternate example 18, the computer-readable storage medium of example 14 is provided, wherein the first and second quantities are sufficiently distinguishable if the equation results in a positive number for at least one fluorescence threshold.

In alternate example 19, the computer-readable storage medium of example 11 is provided, further comprising instructions for: discarding a predetermined number of outliers from the first and second set of $C_t$ values.

In alternate example 20, the computer-readable storage medium of example 11 is provided, wherein the set of fluorescence thresholds includes 90 fluorescence thresholds.

In example 21, a system for validating an instrument is provided. The system comprises: a processor; and a memory configured to store processor-executable instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In alternate example 22, the system of example 21 is provided further comprising instructions for: displaying an indication the instrument is validated if the first and second quantities are sufficiently distinguishable.

In alternate example 23, the system of example 21 is provided, wherein the instruction for calculating if the first and second quantities are sufficiently distinguishable includes determining a mean ($\mu$) and a standard deviation ($\sigma$) of the first and second set of $C_t$ values.

In alternate example 24, the system of example 23 is provided, wherein the first and second quantities are sufficiently distinguishable if the following equation results in a positive number:

$$((\mu C_{tquant1} - 3\sigma C_{tquant1}) - (\mu C_{tquant2} + 3\sigma C_{tquant2})).$$

In alternate example 25, the system of example 21 is provided, wherein the sample is a RNase P gene.

In alternate example 26, the system of example 21 is provided, wherein the first and second quantity are different.

In alternate example 27, the system of example 21 is provided, wherein there is a 2-fold difference between the second quantity and the first quantity.

In alternate example 28, the system of example 24 is provided, wherein the first and second quantities are sufficiently distinguishable if the equation results in a positive number for at least one fluorescence threshold.

In alternate example 29, the system of example 21 is provided, wherein the memory further comprises instructions for: discarding a predetermined number of outliers from the first and second set of $C_t$ values.

In alternate example 30, the system of example 21 is provided, wherein the set of fluorescence thresholds includes 90 fluorescence thresholds.

In example 31, a system for validating an instrument is provided. The system comprises: a PCR instrument interface configured to receive amplification data from a validation plate to generate a plurality of amplification curves, wherein the validation plate includes a sample of a first quantity and a second quantity, and each amplification curve includes an exponential region; a (cycle threshold) $C_t$ calculator configured to: determine a set of fluorescence thresholds based on the exponential regions of the plurality of amplification curves, and determine, for each fluorescence threshold of the set, a first set of $C_t$ values of amplification curves generated from the samples of the first quantity and a second set of $C_t$ values of amplification curves generated from the samples of the second quantity; a $C_t$ database configured to store the first and second set of $C_t$ values for each fluorescence threshold of the set; and a validator configured to calculate if the first and second quantities are sufficiently distinguishable based on $C_t$ values at each of the plurality of fluorescence thresholds.

In alternate example 32, the system of example 31 is provided, further comprising: a display engine configured to display an indication the instrument is validated if the first and second quantities are sufficiently distinguishable.

In alternate example 33, the system of example 31, wherein the validator is further configured to, for calculating if the first and second quantities are sufficiently distinguishable, determine a mean (μ) and a standard deviation (σ) of the first and second set of $C_t$ values.

In alternate example 34, the system of example 33, wherein the validator determines that first and second quantities are sufficiently distinguishable if the following equation results in a positive number:

$$((\mu C_{tquant1} - 3\sigma C_{tquant1}) - (\mu C_{tquant2} + 3\sigma C_{tquant2})).$$

In alternate example 35, the system of example 31, wherein the sample is a RNase P gene.

In alternate example 36, the system of example 31, wherein the first and second quantity are different.

In alternate example 37, the system of example 31, wherein there is a 2-fold difference between the second quantity and the first quantity.

In alternate example 38, the system of example 37, wherein the validator determines that the first and second quantities are sufficiently distinguishable if the equation results in a positive number for at least one fluorescence threshold.

In alternate example 39, the system of example 31, wherein the $C_t$ is further configured to discard a predetermined number of outliers from the first and second set of $C_t$ values.

In alternate example 40, the system of example 31, wherein the set of fluorescence thresholds includes 90 fluorescence thresholds.

In example 41, a method for validating an instrument is provided. The method comprises: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In example 42, a computer-readable storage medium encoded with processor-executable instructions for validating an instrument is provided. The instructions comprise instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In example 43, a system for validating an instrument is provided. The system comprises: a processor; and a memory configured to store processor-executable instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold ($C_t$) values of amplification curves generated from the samples of the first quantity and a second set of $C_t$ values of amplification curves generated from the samples of the second quantity; and calculating if the first and second quantities are sufficiently distinguishable based on $C_t$ values at each of the plurality of fluorescence thresholds.

In example 44, a system for validating an instrument is provided. The system comprises: a PCR instrument interface configured to receive amplification data from a validation plate to generate a plurality of amplification curves, wherein the validation plate includes a sample of a first quantity and a second quantity, and each amplification curve includes an exponential region; a (cycle threshold) $C_t$ calculator configured to: determine a set of fluorescence thresholds based on the exponential regions of the plurality of amplification curves, and determine, for each fluorescence threshold of the set, a first set of $C_t$ values of amplification curves generated from the samples of the first quantity and a second set of $C_t$ values of amplification curves generated from the samples of the second quantity; a $C_t$ database configured to store the first and second set of $C_t$ values for each fluorescence threshold of the set; and a validator configured to calculate if the first and second quantities are sufficiently distinguishable based on $C_t$ values at each of the plurality of fluorescence thresholds.

In example 54, the examples 41, 42, 43, 44, or any of the preceding examples, may further comprise displaying an indication the instrument is validated if the first and second quantities are sufficiently distinguishable.

In example 55, the examples 41, 42, 43, 44, or any of the preceding examples are provided, wherein the calculating if the first and second quantities are sufficiently distinguishable includes determining a mean (μ) and a standard deviation (σ) of the first and second set of $C_t$ values.

In example 56, the examples 41, 42, 43, 44, 55, or any of the preceding examples are provided, wherein the first and second quantities are sufficiently distinguishable if the following equation results in a positive number:

$$((\mu C_{tquant1} - 3\sigma C_{tquant1}) - (\mu C_{tquant2} + 3\sigma C_{tquant2})).$$

In example 57, the examples 41, 42, 43, 44, or any of the preceding examples are provided, wherein the sample is a RNase P gene.

In example 58, the examples 41, 42, 43, 44, or any of the preceding examples are provided, wherein the first and second quantity are different.

In example 59, the examples 41, 42, 43, 44, or any of the preceding examples are provided, wherein there is a 2-fold difference between the second quantity and the first quantity.

In example 60, the examples 41, 42, 43, 44, or any of the preceding examples are provided, wherein the first and second quantities are sufficiently distinguishable if the equation results in a positive number for at least one fluorescence threshold.

In example 61, the examples 41, 42, 43, 44, or any of the preceding examples are provided, further comprising discarding a predetermined number of outliers from the first and second set of $C_t$ values.

In example 62, the examples 41, 42, 43, 44, or any of the preceding examples are provided, wherein the set of fluorescence thresholds includes 90 fluorescence thresholds.

In example 63, the examples 41, 42, 43, 44, or any of the preceding examples are provided, wherein a display engine is configured to display an indication the instrument is validated if the first and second quantities are sufficiently distinguishable.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Although various embodiments have been described with respect to certain exemplary embodiments, examples, and applications, it will be apparent to those skilled in the art that various modifications and changes may be made without departing from the present teachings.

What is claimed is:

1. A method for validating an instrument, the method comprising:
    receiving, at an instrument interface, amplification data from a validation plate, wherein the validation plate includes a sample of a first quantity and a sample of a second quantity;
    generating a plurality of amplification curves based on the received amplification data, wherein each amplification curve includes an exponential region;
    determining a set of fluorescence thresholds based on the exponential regions of the plurality of amplification curves;
    determining, for each fluorescence threshold of the set of fluorescence thresholds, a first set of cycle threshold ($C_t$) values of amplification curves generated from the sample of the first quantity and a second set of $C_t$ values of amplification curves generated from the sample of the second quantity;
    calculating if the first quantity and the second quantity are sufficiently distinguishable by the instrument based on at least a portion of the first set of $C_t$ values and at least a portion of the second set of $C_t$ values;
    displaying an indication of successful validation of the instrument or failed validation of the instrument based on the calculation; and
    in accordance with a successful validation of the instrument, the validated instrument operating to conduct experiments measuring one or more samples.

2. The method of claim 1, wherein the calculating if the first quantity and the second quantity are sufficiently distinguishable includes determining a mean ($\mu$) and a standard deviation ($\sigma$) of the first and second sets of $C_t$ values.

3. The method of claim 2, wherein the first quantity and the second quantities are sufficiently distinguishable if the following equation results in a positive number:

$$((\mu C_{tquant1} - 3\sigma C_{tquant1}) - (\mu C_{tquant2} + 3\sigma C_{quant2})).$$

4. The method of claim 1, wherein the sample of the first quantity and the sample of the second quantity are RNase P samples.

5. The method of claim 3, wherein the first quantity and the second quantity are sufficiently distinguishable if the equation results in a positive number for at least one fluorescence threshold.

6. The method of claim 1, further comprising:
    discarding a predetermined number of outliers from the first and second sets of $C_t$ values.

7. A computer-readable storage medium encoded with processor-executable instructions for validating an instrument, the instructions comprising instructions for:
    receiving, at an instrument interface, amplification data from a validation plate, wherein the validation plate includes a sample of a first quantity and a sample of a second quantity;
    generating a plurality of amplification curves based on the received amplification data, wherein each amplification curve includes an exponential region;
    determining a set of fluorescence thresholds based on the exponential regions of the plurality of amplification curves;
    determining, for each fluorescence threshold of the set of fluorescence thresholds, a first set of cycle threshold ($C_t$) values of amplification curves generated from the sample of the first quantity and a second set of $C_t$ values of amplification curves generated from the sample of the second quantity;
    calculating if the first quantity and the second quantity are sufficiently distinguishable by the instrument based on at least a portion of the first set of $C_t$ values and at least a portion of the second set of $C_t$ values;
    displaying an indication of successful validation of the instrument or failed validation of the instrument based on the calculation; and
    in accordance with a successful validation of the instrument, the validated instrument operating to conduct experiments measuring one or more samples.

8. The computer-readable storage medium of claim 7, wherein the instructions for calculating if the first quantity and the second quantity are sufficiently distinguishable include determining a mean ($\mu$) and a standard deviation ($\sigma$) of the first and second set of $C_t$ values.

9. The computer-readable storage medium of claim 8, wherein the first quantity and the second quantity are sufficiently distinguishable if the following equation results in a positive number:

$$((\mu C_{tquant1} - 3\sigma C_{tquant1}) - (\mu C_{tquant2} + 3\sigma C_{quant2})).$$

10. The computer-readable storage medium of claim 7, wherein the sample of the first quantity and the sample of the second quantity are RNase P samples.

11. The computer-readable storage medium of claim 9, wherein the first quantity and the second quantity are sufficiently distinguishable if the equation results in a positive number for at least one fluorescence threshold.

12. The computer-readable storage medium of claim 7, wherein the set of fluorescence thresholds includes 90 fluorescence thresholds.

13. A system for validating an instrument, the system comprising:
    an instrument interface configured to receive amplification data from a validation plate to generate a plurality of amplification curves, wherein the validation plate includes a sample of a first quantity and a sample of a second quantity, and each amplification curve includes an exponential region;
    a (cycle threshold) Ct calculator configured to:
        determine a set of fluorescence thresholds based on the exponential regions of the plurality of amplification curves, and
        determine, for each fluorescence threshold of the set of fluorescence thresholds, a first set of $C_t$ values of amplification curves generated from the sample of the first quantity and a second set of $C_t$ values of amplification curves generated from the sample of the second quantity;

a validator configured to calculate if the first quantity and the second quantity are sufficiently distinguishable by the instrument based on at least a portion of the first set of $C_t$ values and at least a portion of the second set of $C_t$ values;

a display configured to display an indication of successful validation of the instrument or failed validation of the instrument based on the calculation; and sub-systems of the instrument configured to, in accordance with a successful validation of the instrument, operate to conduct experiments measuring one or more samples.

14. The system of claim 13, wherein the validator is further configured to, for calculating if the first quantity and the second quantity are sufficiently distinguishable, determine a mean ($\mu$) and a standard deviation ($\sigma$) of the first and second sets of $C_t$ values.

15. The system of claim 14, wherein the validator determines that the first quantity and the second quantity are sufficiently distinguishable if the following equation results in a positive number:

$$((\mu C_{tquant1} - 3\sigma C_{tquant1}) - (\mu C_{tquant2} + 3\sigma C_{quant2})).$$

16. The system of claim 13, wherein the sample of the first quantity and the sample of the second quantity are RNase P samples.

17. The system of claim 13, wherein there is a 2-fold difference between the second quantity and the first quantity.

18. The system of claim 15, wherein the validator determines that the first quantity and the second quantity are sufficiently distinguishable if the equation results in a positive number for at least one fluorescence threshold.

19. The system of claim 13, wherein the $C_t$ is further configured to discard a predetermined number of outliers from the first and second sets of $C_t$ values.

20. The system of claim 13, wherein the set of fluorescence thresholds includes 90 fluorescence thresholds.

* * * * *